US012702334B2

(12) United States Patent
Ma et al.

(10) Patent No.: US 12,702,334 B2
(45) Date of Patent: Aug. 11, 2026

(54) CATHETER HAVING DEDICATED BLOOD COLLECTION PORT AND RELATED METHODS

(71) Applicant: Becton, Dickinson and Company, Franklin Lakes, NJ (US)

(72) Inventors: Yiping Ma, Layton, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 710 days.

(21) Appl. No.: 17/143,911

(22) Filed: Jan. 7, 2021

(65) Prior Publication Data

US 2021/0228125 A1 Jul. 29, 2021

Related U.S. Application Data

(60) Provisional application No. 62/965,697, filed on Jan. 24, 2020.

(51) Int. Cl.

| | |
|---|---|
| ***A61B 5/15*** | (2006.01) |
| ***A61M 25/00*** | (2006.01) |
| ***A61M 39/10*** | (2006.01) |

(52) U.S. Cl.
CPC ..... *A61B 5/150992* (2013.01); *A61M 25/003* (2013.01); *A61M 25/0082* (2013.01); *A61M 39/105* (2013.01); *A61M 2025/0037* (2013.01); *A61M 2025/0095* (2013.01); *A61M 2039/1077* (2013.01)

(58) Field of Classification Search
CPC ........ A61B 5/150992; A61B 5/150946; A61B 5/1545; A61B 5/15003; A61B 5/150007; A61B 5/150206; A61B 5/153; A61B 5/14; A61B 5/158; A61M 25/003; A61M 25/0082; A61M 39/105; A61M 2025/0037; A61M 2025/0095; A61M 2039/1077; A61M 25/0606; A61M 2025/0039; A61M 25/0028; A61M 25/0097; A61M 5/158; A61M 5/14; A61M 2005/1587
See application file for complete search history.

(56) References Cited

U.S. PATENT DOCUMENTS

| | | | | |
|---|---|---|---|---|
| 4,016,879 A | | 4/1977 | Mellor | |
| 4,319,582 A | | 3/1982 | Eldridge | |
| 4,409,991 A | | 10/1983 | Eldridge | |
| 4,895,561 A | * | 1/1990 | Mahurkar | A61M 1/3653 604/533 |
| 9,579,485 B2 | | 2/2017 | Oborn et al. | |

(Continued)

FOREIGN PATENT DOCUMENTS

| | | |
|---|---|---|
| AU | 535510 B2 | 3/1984 |
| AU | 2003284115 A1 | 5/2004 |

(Continued)

*Primary Examiner* — Matthew Kremer
*Assistant Examiner* — Nidhi N Patel
(74) *Attorney, Agent, or Firm* — Kirton McConkie; Whitney Blair; Kevin Stinger

(57) ABSTRACT

An extension set for a catheter assembly may include a first lumen coupled to an infusion port and a second lumen coupled to a blood collection port. The second lumen may include a flow resistance that is optimized to reduce hemolysis during blood collection.

9 Claims, 5 Drawing Sheets

(56) References Cited

U.S. PATENT DOCUMENTS

2002/0107506 A1* 8/2002 McGuckin, Jr. .. A61M 25/0194 604/523
2005/0043709 A1 2/2005 Brimhall et al.
2006/0206048 A1* 9/2006 Loggie .............. A61M 25/0026 604/8
2007/0250021 A1 10/2007 Brimhall et al.
2007/0250037 A1 10/2007 Brimhall et al.
2011/0009717 A1 1/2011 Davis et al.
2013/0121897 A1* 5/2013 Davis ............... A61B 5/150221 422/549
2016/0038067 A1 2/2016 Davis et al.
2018/0140240 A1 5/2018 Bullington et al.
2018/0344908 A1* 12/2018 Hiemenz ............. A61M 3/0241
2019/0021640 A1 1/2019 Burkholz et al.
2019/0022367 A1 1/2019 Burkholz et al.
2019/0105464 A1 4/2019 Kumar et al.
2019/0247630 A1* 8/2019 Brenizer ............. A61M 31/005
2019/0307989 A1 10/2019 Ma et al.
2019/0321590 A1 10/2019 Burkholz et al.
2019/0321599 A1 10/2019 Burkholz et al.
2019/0374144 A1 12/2019 Langdell et al.
2019/0374145 A1 12/2019 Breindel et al.
2021/0228125 A1 7/2021 Ma

FOREIGN PATENT DOCUMENTS

AU 2010271420 A1 2/2012
AU 2018303661 A1 2/2020
AU 2019256311 A1 11/2020
AU 2019282769 A1 1/2021
AU 2021211372 A1 8/2022
BR 8008284 A 8/1981
BR 112012000396 A2 7/2017
BR 112020001073 A2 7/2020
BR 112020021351 A2 1/2021
CA 3070065 A1 1/2019
CA 3096428 A1 10/2019
CN 102573629 A 7/2012
CN 110141255 8/2019
CN 111132719 A 5/2020
CN 112154005 A1 12/2020
EP 0033528 A1 8/1981
EP 1572262 A2 9/2005
EP 2451353 A2 5/2012
EP 3541284 A1 9/2019
EP 3655083 A2 5/2020
EP 3781247 A2 2/2021
EP 3813668 A2 5/2021
EP 4093284 A1 11/2022
ES 265372 U 12/1982
ES 2342376 T3 7/2010
ES 2467142 T3 6/2014
JP S56109643 A2 8/1981
JP H07275364 A 10/1995
JP 2007089768 A 4/2007
JP 2008515483 A 5/2008
JP 2008529674 A 8/2008
JP 2012532683 A 12/2012
JP 5628310 B2 11/2014
JP 2018023632 A 2/2018
JP 6529905 B2 6/2019
JP 2019530521 A 10/2019
JP 2020528312 A 9/2020
KR 20160088422 A 7/2016
KR 101849180 B1 4/2018
KR 20200030095 A 3/2020
KR 20210003817 A 1/2021
MX 151668 A 1/1985
NZ 195456 A 11/1982
SG 11202000409 Y 2/2020
SG 11202009892 R 11/2020
WO 2004/032995 4/2004
WO 2011005956 A2 1/2011
WO 2017164223 A1 9/2017
WO 2018094310 A1 5/2018
WO 2019018473 A2 1/2019
WO 2019204413 A2 10/2019
WO 2019/236956 12/2019
WO 2021150400 A1 7/2021

* cited by examiner

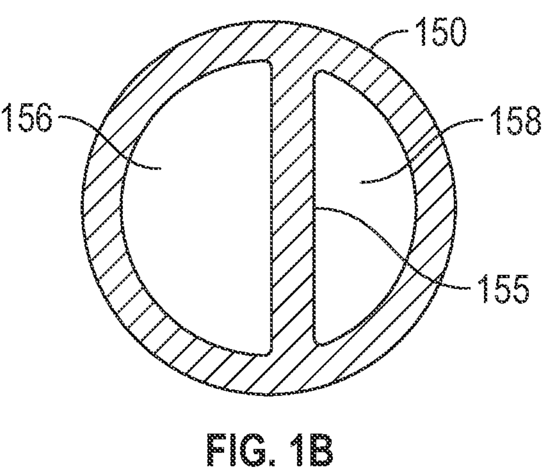
FIG. 1B
150
157
156
158
FIG. 1C
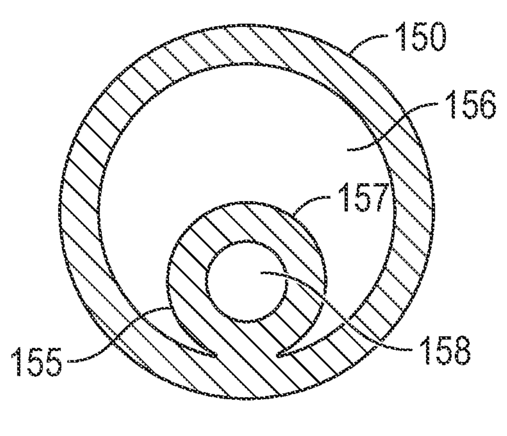
FIG. 1D 200
251
270
254a
250a
258
250b
254b
260
256
240
152b
224
152a
220
222
230
242
244

300
350a
354
380
360
340
324
352
320
322
350b
330
370
342
344

CATHETER HAVING DEDICATED BLOOD COLLECTION PORT AND RELATED METHODS

RELATED APPLICATIONS

This application claims the benefit of U.S. Provisional Application No. 62/965,697, filed Jan. 24, 2020, and entitled CATHETER HAVING DEDICATED BLOOD COLLECTION PORT AND RELATED METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may be an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood samples are commonly collected from a patient via an IV catheter. A syringe and needle may be used to collect a blood sample from the patient's IV catheter. Additionally, an evacuated blood collection tube may be used. These devices are typically coupled to a catheter adapter of the IV catheter such that the device may draw blood from the patient via the IV catheter set. In some instances, the blood collection device directly accesses the catheter adapter housing, such as via a y-port or other access point. In other instances, the catheter adapter housing includes an extension tube having an access port, wherein the extension tube is in fluid communication with the inner lumen of the catheter adapter housing. These various access points provide fluid pathways by which any type of fluid may be move into, or drawn out of the catheter adapter of the IV catheter. As a result of this comprehensive design, a clinician must use precise care to control the flow rate of shear-sensitive fluids through these various access points. If the clinician is unable to maintain a safe flow rate while drawing or infusing a shear-sensitive fluid, it is likely that the fluid may be damaged. For example, red blood cells are highly susceptible to hemolysis due to high shear stress state during the process of drawing or infusing blood via an IV catheter. Hemolysis may result in rejection and discard of a blood sample. High flow rates may also cause high pressure differential that can result in catheter tip collapse, vein collapse, or other complications that prevent or restrict blood from being collected.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to an extension set for a vascular access device, as well as related devices, systems, and methods. In some embodiments, a vascular access system may include the extension set coupled to a catheter adapter having an intravenous catheter and a needle assemble for accessing a vascular system.

In some embodiments, the extension set includes an integrated peripheral intravenous catheter with a dedicated blood collection port. The blood collection port is connected to an optimized fluid path configured to minimize the likelihood of hemolysis. In some embodiments, in the present disclosure, optimized may mean designed to improve. Hemolysis is minimized by configuring the optimized fluid path to have fluidic or flow resistance and/or a flow rate that matches or is comparable to the maximum shear stress of a typical blood collection needle set. As such, blood that is collected through the optimized fluid path is substantially or completely protected from hemolysis. In many instances, the optimized fluidic or flow resistance is dependent upon catheter gauge size. In some instances, the optimized fluid or flow resistance of a dedicated blood collection port results in a flow rate that is undesirable and/or incompatible for infusing non-shear sensitive fluids. Accordingly, various embodiments of the present disclosure include dedicated blood collection and infusion ports. Therefore, the features of the present disclosure provide ease of operation such that there is no need to locate the best fluid resistance or flow rate for blood collection.

In some embodiments, an extension set is provided including a single extension tube coupled to a catheter adapter, wherein the single extension tube includes a first lumen optimized for blood collection, and a second lumen optimized for infusion, wherein a flow resistance of the first lumen is greater than a flow resistance of the second lumen. As such, a clinician is prevented from drawing blood through the first lumen at a flow rate that results in hemolysis. The first lumen is coupled to a blood collection port, and the second lumen is coupled to an infusion port. The flow resistances of the first and second lumen and optimized by selecting the catheter or lumen gauges of the respective lumens. In some instances, the first lumen (i.e., the lumen coupled to the blood collection port and optimized for blood collection) includes a cross-section area that is less than the second lumen (i.e., the lumen coupled to the infusion port and optimized for infusion).

In some embodiments, an extension set is provided including first and second extension tubes coupled to a catheter adapter, wherein the first extension tube includes a lumen optimized for blood collection, and the second extension tube includes a lumen optimized for infusion, wherein the first extension tube is coupled to a blood collection port, and the second extension tube is coupled to an infusion port.

In some embodiments, an extension set is provided including a y-port coupled to a catheter adapter via a first extension tube, wherein the y-port includes an infusion port having a flow resistance optimized for infusion, and wherein the y-port further includes a luer adapter for selectively receiving a second extension tube having a blood collection port, wherein the second extension tube includes a flow resistance optimized for blood collection.

In some embodiments, an extension set of the present disclosure is provided as an integral component of a catheter assembly. In other embodiments, an extension set of the present disclosure is provided as a separate unit that is configured for selective attachment to a catheter assembly, such as a catheter adapter of an intravenous catheter assembly, such that the lumens of the extension set are in fluid communication with an interior lumen of the catheter adapter.

It is to be understood that both the foregoing general description and the following detailed description are examples and explanatory and are not restrictive of the present disclosure, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1B is a cross-sectional view of a dual lumen extension tube, wherein one of the lumens is optimized for blood collection in accordance with a representative embodiment of the present disclosure;

FIG. 1C is a cross-sectional view of a dual lumen extension tube, wherein one of the lumens is optimized for blood collection in accordance with a representative embodiment of the present disclosure;

FIG. 1D is a cross-sectional view of a dual lumen extension tube, wherein one of the lumens is optimized for blood collection in accordance with a representative embodiment of the present disclosure;

FIG. 3 is a top view of a catheter assembly including an extension set having a y-port including an infusion port, and further including an extension tube having a blood collection port, wherein the extension tube is optimized for blood collection in accordance with a representative embodiment of the present disclosure; and.

DETAILED DESCRIPTION

Figure 1A:
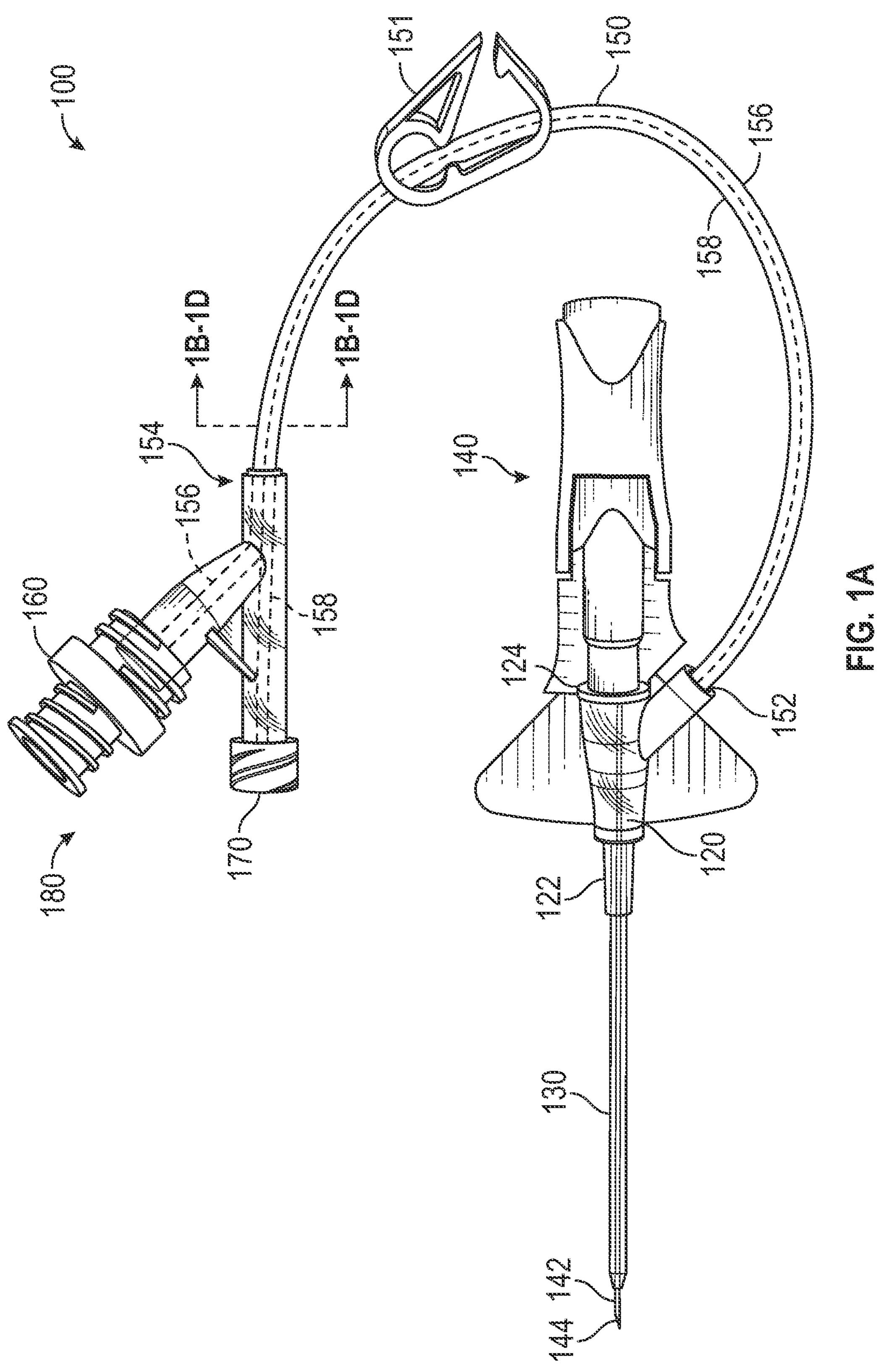
FIG. 1A is a top view of a catheter assembly including an extension set having a dual lumen extension tube, wherein one of the lumens is optimized for blood collection in accordance with a representative embodiment of the present disclosure.

Referring now to FIG. 1, a catheter assembly 100 is illustrated. Catheter assembly 100 is illustrated as a peripheral intravenous catheter, however the aspects of the present disclosure may implemented in various other types of intravenous catheters and catheter assemblies, as will be readily appreciated by one having ordinary skill in the art. For example, aspects of the present disclosure may be incorporated into or otherwise implemented in the BD NEXIVATM Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable catheter assembly. In some embodiments, catheter assembly 100 may include a peripheral intravenous catheter (PIVC), a peripherally inserted central catheter (PICC), or a midline catheter. Catheter assembly 100 includes a catheter adapter 120 having a distal end 122 including a catheter 130. Catheter assembly 100 further includes a proximal end 124 configured to receive a needle assembly 140 having an introducer needle 142 that is threaded through catheter adapter 120 and catheter 130 such that a sharpened distal tip 144 of introducer needle 142 is exposed prior to catheterization. Catheter adapter 120 further includes an interior lumen in fluid communication with catheter 30. The various materials of catheter adapter 120, catheter 130, and needle assembly 140 are well known in the art.

Catheter assembly 100 further includes an extension tube 150 having a first end 152 coupled to catheter adapter 120, and a second end 154 having an infusion port 160 and a blood collection port 170. In some embodiments, extension tube 150 is a multi-lumen tube including a first lumen 156 in fluid communication with the infusion port 160, and a second lumen 158 in fluid communication with the blood collection port 170. In some embodiments, infusion port 160 and blood collection port 170 include a y-port 180, wherein ports 160 and 170 are the two legs of the y-port. In some instances, y-port 180 includes luer adapters configured to selectively receive infusion port 160 and blood collection port 170 as separate units. In other instances, at least one of infusion port 160 and blood collection port 170 is an integral component of y-port 180.

First and second lumens 156 and 158 include separate fluid pathways along the length of extension tube 150, wherein the separate fluid pathways converge in the interior lumen of catheter adapter 120. In some embodiments, extension tube 50 further includes a clamp 151 that may be selectively engaged to control fluid flow through first and/or second lumens 156 and 158.

First and second lumens 156 and 158 each include a fluidic or flow resistance that is a function of the fluid pathway diameter, the cross-sectional area of the respective fluid pathways, and/or the length of extension tube 150. In some embodiments, a flow resistance of the first and/or second lumen 156 and 158 is optimized to act as a flow resistor for catheter assembly 100. For example, a flow resistance of the first lumen 156 may be optimized for infusion, while a flow resistance of the second lumen 158 may be optimized for blood collection, wherein the optimization for blood collection minimized hemolysis. In some embodiments, a flow resistance of the second lumen is more than a flow resistance of the first lumen. In some embodiments, a flow resistance of the second lumen is optimized to reduce hemolysis, and a flow resistance of the first lumen is less than the flow resistance of the second lumen.

Blood cells experience shear stress as they flow in a fluid pathway. In a fluid pathway, maximum shear stress occurs along the wall of the fluid pathway, and is referred to as "wall shear stress". Wall shear stress on blood cells is considered a major source of mechanical damage to blood cells, often resulting in hemolysis. For cylindrical fluid path, the wall shear stress is typically expressed as:

$$T = \frac{1}{2} \cdot \frac{\Delta p}{L} \cdot (kr)$$

in which ΔP is the pressure drop along a path with a length of L and an interior radius of r. k is shrinkage index.

To fill a certain volume of collection tube, V, with a flow rate of Q, the time needed can be simply assessed by:

$$t = \frac{v}{Q} = 8\mu v \cdot \frac{1}{\pi r^4} \Big/ \left(\frac{\Delta p}{L}\right)$$

in which μ is the dynamic viscosity of the fluid. Hemolysis is typically associated with both the wall shear stress and the time a blood cell is exposed to wall shear stress. From literature, it has been widely considered that hemolysis index can be approached as a function of:

$$HI(\%) = A * t^{\alpha} * T^{\beta}$$

in which A, α, and β are coefficients.

In principle, the hemolysis index is related to pressure gradient and cross-sectional characteristic dimension:

$$HI(\%) \propto \left(\frac{\Delta P}{l}\right)^{\beta-\alpha} \cdot \left(\frac{1}{r}\right)^{4\alpha-\beta}$$

In some embodiments, a length of extension tube 150 may be selected based on one or more of the following: a gauge of a particular lumen of the extension tube, a particular catheter assembly configuration, or a clinical setup. In some embodiments, extension tube 150 may have a length (L) from first end 152 to second end 154. In some embodiments, a flow resistance of a lumen of extension tube 150 may be optimized to reduce the shear wall stress, and corresponding hemolysis, experienced by red blood cells flowing therethrough. For example, in some embodiments a lumen of extension tube 150 includes an inner diameter (D) selected such that $D^4/L$ provides a lumen volume equal to or less than 0.27E-06 cubic inches, equal to or less than 2.77E-06 cubic inches, equal to or less than 3.24E-07 cubic inches, equal to or less than 3.20E-07 cubic inches, or equal to or less than 6.73E-08 cubic inches, which may reduce the wall shear stress to reduce hemolysis. In some embodiments, $D^4/L$ may be another value.

Referring now to FIGS. 1B-1D, in some embodiments extension tube 150 includes a single multi-lumen tube having a first lumen 156 and a second lumen 158, wherein a cross-section area of the first lumen 156 is greater than a cross-section area of the second lumen 158. In some embodiments, first and second lumens 156 and 158 are divided or separated by an interior wall 155 of extension tube 150. In some embodiments, second lumen 158 is positioned within first lumen 156, wherein first and second lumens 156 and 158 are separated by a side wall 157 defining second lumen 158. In some embodiments, side wall 157 is concentrically positioned within first lumen 156, as illustrated in FIG. 1C. In some embodiments, side wall 157 is a portion of interior wall 155 such that second lumen is positioned within first lumen 156 and in contact with the inner wall surface of the first lumen 156, as illustrated in FIG. 1D. One having ordinary skill in the art will appreciate that first and second lumens 156 and 158 may include additional shapes, configurations, and cross-section areas compatible for use with the features of the present disclosure.

Figure 2:
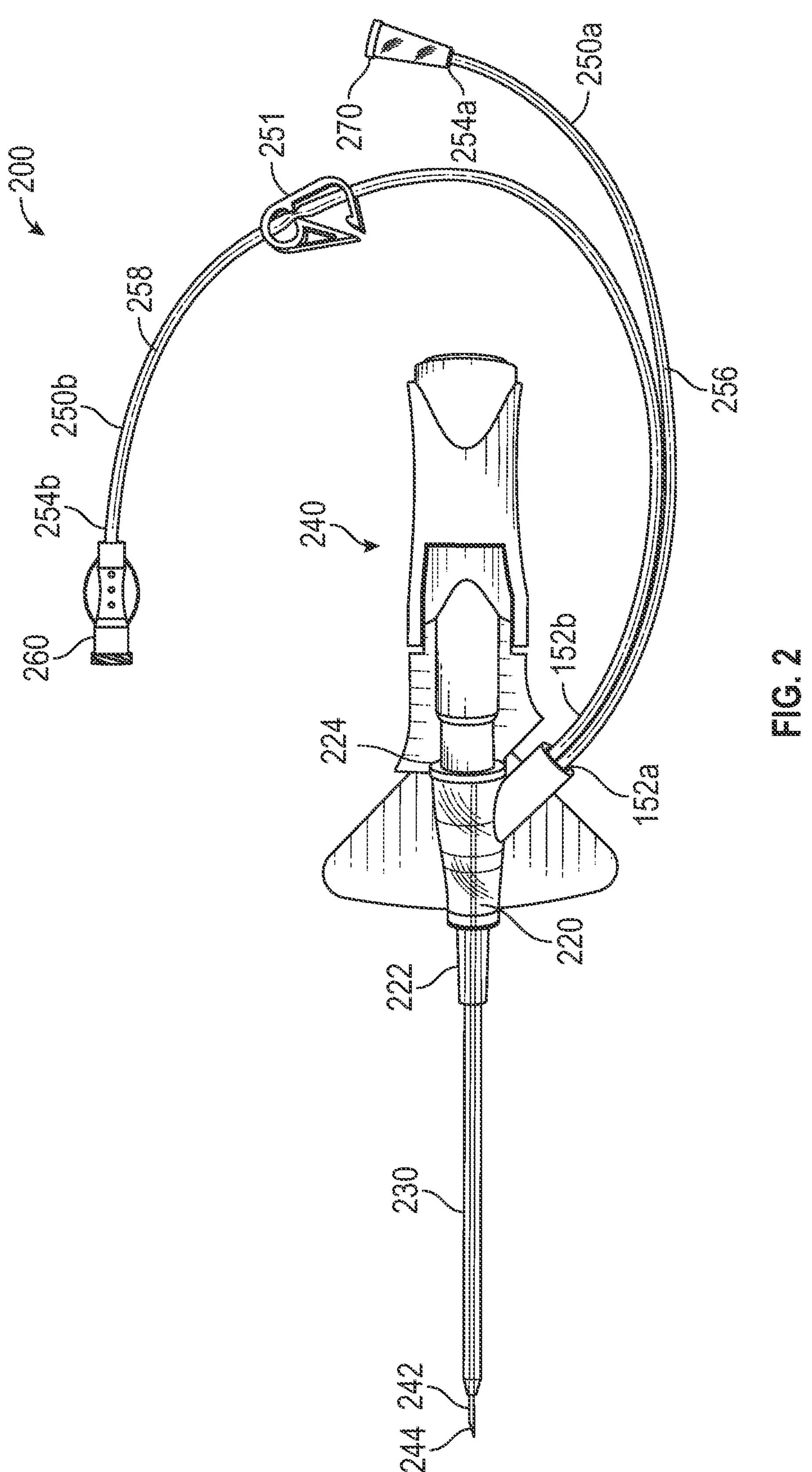
FIG. 2 is a top view of a catheter assembly including an extension set having two extension tubes, wherein one of the extension tubes is optimized for blood collection in accordance with a representative embodiment of the present disclosure.

Referring now to FIG. 2, a catheter assembly 200 is illustrated. Catheter assembly 200 may include any catheter system or suitable catheter assembly disclosed herein. Catheter assembly 200 may further include any additional elements or features of any catheter assembly disclosed herein that is compatible with the embodiment illustrated.

Catheter assembly 200 includes a first extension tube 250*a* having a first end 252*a* coupled to catheter adapter 220, and a second end 254*a* having an infusion port 260. Catheter assembly 200 further includes a second extension tube 250*b* having a first end 252*b* coupled to catheter adapter 220, and a second end 254*b* having a blood collection port 270. First extension tube 250*a* includes a first lumen 256 having a flow resistance optimized for use with infusion procedures. Second extension tube 250*b* include a second lumen 258 having a flow resistance optimized for use with blood collection, wherein the flow resistance of the second lumen 258 reduces, eliminates, or otherwise prevents hemolysis during a blood withdraw. First and second lumens 256 and 258 include separate fluid pathways along their respective extension tubes 250*a* and 250*b*, where the separate fluid pathways converge in the interior lumen of catheter adapter 220. In some embodiments, at least one of first and second extension tubes 250*a* and 250*b* further include a clamp 251 that may be selectively engaged to control fluid flow through first and/or second lumens 256 and 258.

First and second lumens 256 and 258 each include a flow resistance, as discussed above. In some embodiments, second extension tube 205*b* includes a flow resistance optimized to reduce sheer wall stress experienced by red blood cells during blood collection via blood collection port 270. Accordingly, catheter assembly 200 includes an extension tube 250*b* that is dedicated for blood collection. In some embodiments, a length of extension tube 250*b* may be selected based on one or more of the following: a gauge of a particular lumen of the extension tube, a particular catheter assembly configuration, or a clinical setup. In some embodiments, extension tube 250*b* may have a length (L) from first end 252*b* to second end 254*b*. In some embodiments, a flow resistance of a lumen of extension tube 250*b* may be optimized to reduce the shear wall stress, and corresponding hemolysis, experienced by red blood cells flowing therethrough. For example, in some embodiments a lumen of extension tube 250*b* includes an inner diameter (D) selected such that $D^4/L$ provides a lumen volume equal to or less than 0.27E-06 cubic inches, equal to or less than 2.77E-06 cubic inches, equal to or less than 3.24E-07 cubic inches, equal to or less than 3.20E-07 cubic inches, or equal to or less than 6.73E-08 cubic inches, which may reduce the wall shear stress to reduce hemolysis. In some embodiments, $D^4/L$ may be another value.

Figure 3:
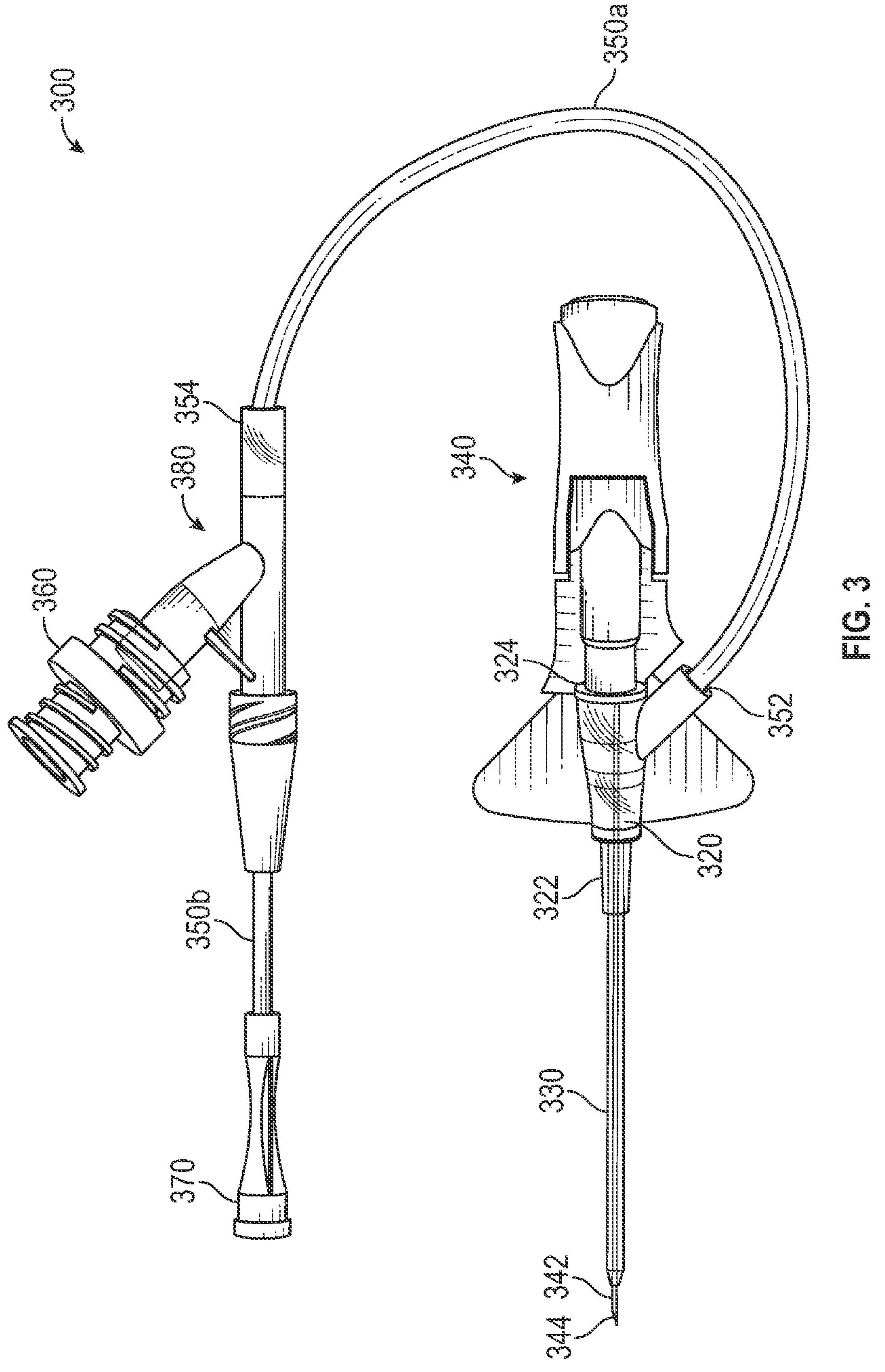
Figure 4:
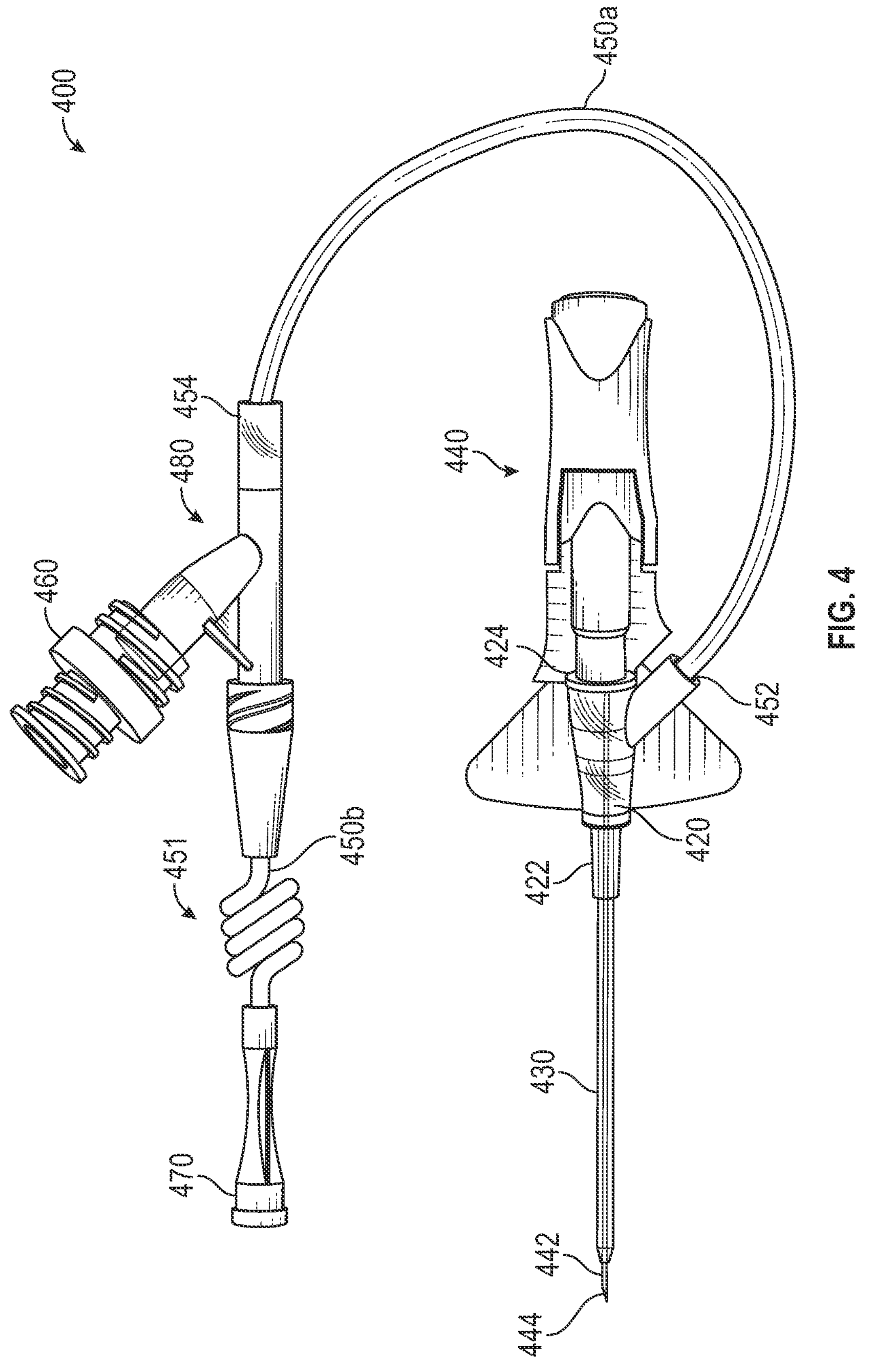
FIG. 4 is a top view of a catheter assembly including an extension having a non-linear portion configured to increase flow resistance within the catheter assembly to distribute the pressure differential and thereby reduce shear stress of a fluid flowing therethrough in accordance with a representative embodiment of the present disclosure.

Referring now to FIG. 3, a catheter assembly 300 is illustrated. Catheter assembly 300 may include any catheter system or suitable catheter assembly disclosed herein. Catheter assembly 200 may further include any additional elements or features of any catheter assembly disclosed herein that is compatible with the embodiment illustrated.

Catheter assembly 300 includes a first extension tube 350*a* having a first end 352*a* coupled to a catheter adapter

320, and a second end 354*a* having an infusion port 360. In some embodiments, infusion port 360 includes a y-port 380, in accordance with one or more embodiments provided herein. First extension tube 350*a* includes a flow resistance that is optimized for infusing a fluid. Accordingly, in some embodiments the flow resistance of first extension tube 350*a* is minimal. In some embodiments, infusion port 360 is selectively coupled to a luer adapter of y-port 380. In other embodiments, infusion port 360 is an integral component of y-port 380. In some embodiments, a flow resistance of first extension tube 350*a* is equal to a flow resistance of y-port 380 and infusion port 360.

Catheter assembly 300 further includes a second extension tube 350*b* having a first end 352*b* coupled to y-port 380, and a second end 354*b* having a blood collection port 370. Second extension tube 350*b* includes a flow resistance that is optimized for collecting a blood sample, wherein the flow resistance minimizes sheer wall stress and reduces, limits or eliminates hemolysis.

In some embodiments, second extension tube 350*b* is selectively coupled to a luer adapter of y-port 380, such that a second extension tube 350*b* may be exchanged with an additional extension tube having an optimized flow resistance. In some embodiments, a gauge of second extension tube 350*b* is selected to match flow resistance of catheter 330, wherein second extension tube 350*b* may be replaced with a desired gauge in order to optimize a flow resistance of blood collection port 370 and the entire catheter assembly. In some embodiments, a flow resistance of first extension tube 350*a* is less than a flow resistance of catheter 330, and less than a flow resistance of second extension tube 350*b*.

Various or any of the catheter assemblies of the present disclosure may include additional features and elements configured to reduce shear stress experienced by red blood cells while collecting a blood sample. Non-limiting examples of such additional features and elements are disclosed in U.S. Provisional Application Ser. No. 62/965,674, entitled "BLOOD COLLECTION ADAPTER AND RELATED DEVICES TO REDUCE HEMOLYSIS," filed Jan. 24, 2020, which is incorporated herein in its entirety. For example, in some embodiments a second extension tube 450*b* of catheter assembly 400 may include a non-linear portion such as a spiral, a coil shape, an S-shape, or another suitable non-linear shape. The non-linear portion may facilitate increased flow resistance within the catheter assembly to distribute the pressure differential and thereby reduce shear stress experienced by red blood cells. In some embodiments, no fluid flowing through non-linear portion 451 may flow in a straight or linear pattern. In some embodiments, non-linear portion 451 may increase a length of the fluid pathway of second extension tube 450*b* and thereby may increase flow resistance and decrease blood flow within catheter assembly. Accordingly, these embodiments may further reduce a risk of hemolysis during blood collection.

In some embodiments, the extension tubes of the present disclosure may be provided as individual catheter extension sets, separate and apart from a catheter adapter of other components of a catheter assembly. For example, in some embodiments an extension tube of the present disclosure is selectively coupled to a catheter adapter via a slip fit or a leur adapter. Accordingly, the present disclosure further includes catheter extension sets in accordance with the various features and elements described above in connection with the various embodiments.

All examples and conditional language recited herein are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

We claim:

1. A catheter assembly, comprising:

a catheter adapter having a distal end comprising an intravenous catheter, a proximal end configured to receive a needle assembly, and an interior lumen extending therebetween; and a first lumen and a second lumen;

an extension tube, wherein the first lumen and the second lumen extend through the extension tube, the first lumen and the second lumen being in fluid communication with the interior lumen at a first end of the extension tube;

a y-port comprising:

an infusion port, wherein the first lumen extends through the infusion port; and a blood collection port, wherein the second lumen extends through the blood collection port, wherein the first lumen extends between the catheter adapter and the infusion port, wherein the second lumen extends between the catheter adapter and the blood collection port, wherein the first lumen and the second lumen extend through the y-port as mutually isolated fluid pathways such that the first lumen and the second lumen are entirely fluidically separated from each other within the y-port.

2. The catheter assembly of claim 1, wherein a flow resistance of the second lumen is greater than a flow resistance of the first lumen.

3. The catheter assembly of claim 1, wherein a cross-section area of the first lumen is greater than a cross-section area of the second lumen.

4. The catheter assembly of claim 1, wherein the extension tube consists of a single tube comprising the first and second lumens.

5. The catheter assembly of claim 4, wherein the second lumen is positioned within the first lumen within the extension tube.

6. The catheter assembly of claim 4, wherein the first lumen is positioned within the second lumen within the extension tube.

7. The catheter assembly of claim 4, wherein the first lumen and second lumen are separated by an interior wall of the single tube.

8. The catheter assembly of claim 7, wherein the interior wall is a sidewall of the first or second lumen.

9. The catheter assembly of claim 1, wherein a flow resistance of the second lumen is configured to minimize hemolysis.

* * * * *